US010365238B2

(12) United States Patent
Jung

(10) Patent No.: US 10,365,238 B2
(45) Date of Patent: Jul. 30, 2019

(54) DIESEL FUEL QUALITY INSPECTION APPARATUS AND INSPECTION METHOD THEREOF

(71) Applicant: Hyundai Motor Company, Seoul (KR)

(72) Inventor: Jang-Hyun Jung, Suwon-si (KR)

(73) Assignee: Hyundai Motor Company, Seoul (KR)

( * ) Notice: Subject to any disclaimer, the term of this patent is extended or adjusted under 35 U.S.C. 154(b) by 308 days.

(21) Appl. No.: 15/372,144

(22) Filed: Dec. 7, 2016

(65) Prior Publication Data

US 2018/0073998 A1    Mar. 15, 2018

(30) Foreign Application Priority Data

Sep. 13, 2016 (KR) .................. 10-2016-0117860

(51) Int. Cl.

| *G01R 27/28* | (2006.01) |
|---|---|
| *G01N 27/02* | (2006.01) |
| *G01N 33/22* | (2006.01) |
| *G01R 27/26* | (2006.01) |
| *G01R 15/18* | (2006.01) |
| *G01R 19/00* | (2006.01) |
| *G01R 29/08* | (2006.01) |
| *G01R 21/00* | (2006.01) |

(52) U.S. Cl.
CPC .......... *G01N 27/025* (2013.01); *G01N 33/22* (2013.01); *G01R 15/181* (2013.01); *G01R 19/0092* (2013.01); *G01R 21/00* (2013.01); *G01R 27/2611* (2013.01); *G01R 29/0814* (2013.01); *G01R 27/26* (2013.01); *G01R 27/2605* (2013.01)

(58) Field of Classification Search
CPC ............ G01R 27/2611; G01R 19/0092; G01R 15/181; G01R 29/0814; G01R 21/00; G01R 27/26; G01R 27/2605
USPC .................. 324/76.11–76.83, 600, 649, 654
See application file for complete search history.

(56) References Cited

U.S. PATENT DOCUMENTS

| 2009/0289005 A1* | 11/2009 | Bae ........................ F02M 37/22 |
|---|---|---|
| | | 210/416.4 |
| 2016/0138538 A1* | 5/2016 | Ham .................... B01D 35/005 |
| | | 210/96.1 |
| 2016/0305595 A1* | 10/2016 | Iden ...................... F16L 55/168 |

FOREIGN PATENT DOCUMENTS

| JP | H03-269350 A | 11/1991 |
|---|---|---|
| JP | 2009-184475 A | 8/2009 |
| KR | 10-2004-0009438 A | 1/2004 |
| KR | 10-2006-0094357 A | 8/2006 |
| KR | 10-0666134 B1 | 1/2007 |
| KR | 20080053601 A | 6/2008 |
| KR | 10-2016-0062421 A | 6/2016 |

* cited by examiner

*Primary Examiner* — Giovanni Astacio-Oquendo
*Assistant Examiner* — Raul J Rios Russo
(74) *Attorney, Agent, or Firm* — Morgan, Lewis & Bockius LLP

(57) ABSTRACT

A diesel fuel quality inspection apparatus, which is mounted to a lower end portion of a moisture storing part coupled to a lower portion of the filter portion and a filter portion for filtering foreign materials contained to fuel for inspecting moisture contained to diesel fuel to identify quality of fuel may include a body portion coupled to a lower end portion of the moisture storing part, a guide portion formed with a hollow type circular cylinder shape on a bottom surface in the body portion, and a first inspection portion formed to be fixed with a predetermined height in the guide portion.

15 Claims, 5 Drawing Sheets

DIESEL FUEL QUALITY INSPECTION APPARATUS AND INSPECTION METHOD THEREOF

CROSS-REFERENCE TO RELATED APPLICATION

The present application claims priority to Korean Patent Application No. 10-2016-0117860 filed on Sep. 13, 2016, the entire contents of which is incorporated herein for all purposes by this reference.

BACKGROUND OF THE INVENTION

Field of the Invention

The present invention relates to a diesel fuel quality inspection apparatus and an inspection method thereof, and more particularly, to a diesel fuel quality inspection apparatus and an inspection method thereof configured for inspecting diesel fuel quality with measuring change of output voltage by change of magneto-inductance of a coil member which is mounted to be positioned in a fuel filter and is wound so that fuel is positioned therein.

Description of Related Art

A diesel engine is an internal combustion engine making diesel to fuel and has been widely used in various fields such as industry, vessel and vehicle, and so on, as it has merits of high thermal efficiency and lower fuel costs, and so on. The diesel engine has been steadily improving in its output through improvement of fuel injection method and engine rotation method, and so on, and in soot reduction, and so on.

However, since a large amount of impurities and moisture is contained in the diesel fuel, it requires a filtering process removing impurities and moisture remove before supplying the diesel fuel to the diesel engine, such that a fuel filter has been mounted and used for filtering.

In case that bad diesel fuel containing excessive moisture is supplied to the diesel engine, the problems of excessive corrosion and starting off, and so on, may be occurred.

Therefore, European EN590 regulation (moisture content less than 0.02%) to diesel fuel as well as national moisture limits have been fixed, but regulatory situation to this was lacked.

As shown in FIG. 1, a system, which warns the driver when the moisture amount collected in the diesel fuel filter corresponds to moisture collection limits, has been present.

However, there was not the means for detecting fuel quality when bad fuel is supplied to the diesel engine and warning the driver, and so on.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a device having advantages of preventing problems such as failing start, damaging related components, and generating soot according to faulty fuel injection beforehand by detecting faulty fuel and then warning it to a person such as a driver through a warning lamp, as an inspection apparatus including a wound coil is mounted in a fuel filter to inspect change of output voltage depending on change of inductance.

A diesel fuel quality inspection apparatus according to an exemplary embodiment of the present invention may be a diesel fuel quality inspection apparatus which is mounted to a lower end portion of a moisture storing part coupled to a lower portion of the filter portion and a filter portion for filtering foreign materials contained to fuel for inspecting moisture contained to diesel fuel to identify quality of fuel, and the diesel fuel quality inspection apparatus may include a body portion coupled to a lower end portion of the moisture storing part; a guide portion formed with a hollow type circular cylinder shape on a bottom surface in the body portion; and a first inspection portion formed to be fixed with a predetermined height in the guide portion.

In addition, the first inspection portion may include a coil member wound along an inside circumference of the guide portion.

In addition, amount of the coil member being magnetized may be to be different depending on quality of fuel positioned inside the wound coil member.

In addition, the diesel fuel quality inspection apparatus may further include a circuit portion mounted in the body portion to measure change of output voltage depending on change of magneto-inductance of the coil member.

In addition, both end portions of the coil may be respectively connected with the circuit portion.

In addition, the diesel fuel quality inspection apparatus may further include a control portion determining whether to transmit a warning message depending on change of output voltage measured from the circuit portion.

In addition, the guide portion may include at least one opening portion configured such that fuel or moisture is communicated into the guide portion.

In addition, the circuit portion may include a MOSFET-switch once repeating on or off per one second.

In addition, a power source of an outside battery may be connected with the circuit portion.

In addition, the diesel fuel quality inspection apparatus may be mounted in the guide portion and may further include a second inspection portion configured so that a first end thereof is electrically connected with a circuit portion which is mounted in the body portion and a current carrying portion is positioned at a second end thereof.

In addition, the current carrying portion may be formed to be positioned as a predetermined height apart from the circuit portion, and the circuit portion may generate a moisture warning signal as the current carrying portion carries current during being contacted with a water surface of moisture collected to the moisture storing part.

A diesel fuel quality inspection method according to another exemplary embodiment of the present invention may be a diesel fuel quality inspection method for inspecting quality of fuel by amount of moisture contained to fuel, and the diesel fuel quality inspection method may include starting an inspection logic at an on time by performing on or off of a MOSFET-switch per one second; predetermining an optional limit value a % about change of inductance of a coil member; checking a battery voltage; determining a voltage value when inductance is changed as the a %; measuring an output voltage; determining whether the output voltage exceeds the determined voltage value; deciding normal fuel in a case that the output voltage is lower than or same to the determined voltage value according to the result of the determination; and deciding faulty fuel in a case that the measured output voltage is more than the determined voltage value according to the result of the determination.

In addition, amount of the coil member being magnetized may be changed depending on quality of fuel positioned inside the wound coil member.

In addition, the value may be predetermined depending on amount of moisture allowed in diesel fuel.

In addition, the diesel fuel quality inspection method may further include transmitting a warning message in a case of deciding faulty fuel.

a diesel fuel quality inspection apparatus and an inspection method thereof using change of magneto-inductance according to an exemplary embodiment of the present invention has effects of preventing problems including failing start, damaging related components, and generating soot according to faulty fuel injection beforehand by detecting faulty fuel and then warning it to a person including a driver through a warning lamp, as an inspection apparatus including a wound coil is mounted in a fuel filter to inspect change of output voltage depending on change of inductance.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
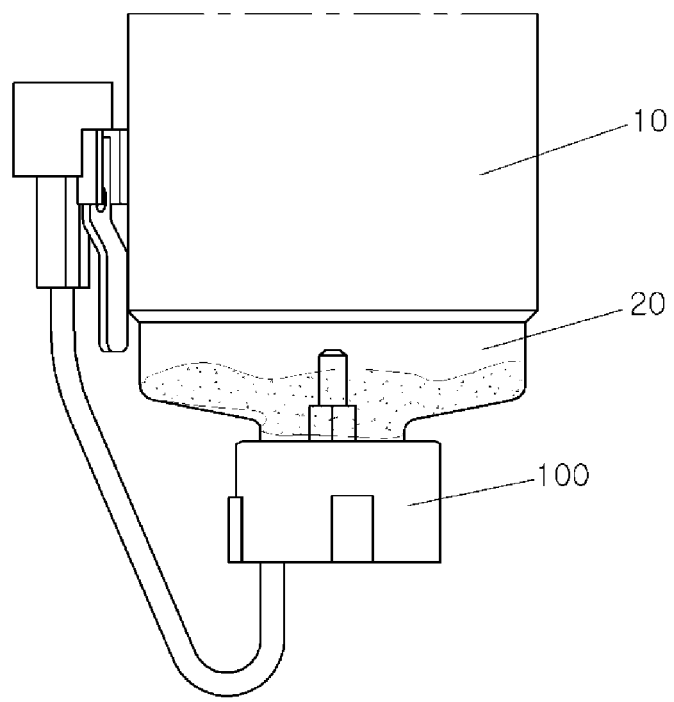
FIG. 1 is a drawing illustrating a diesel fuel filter according to a conventional art.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Figure 2:
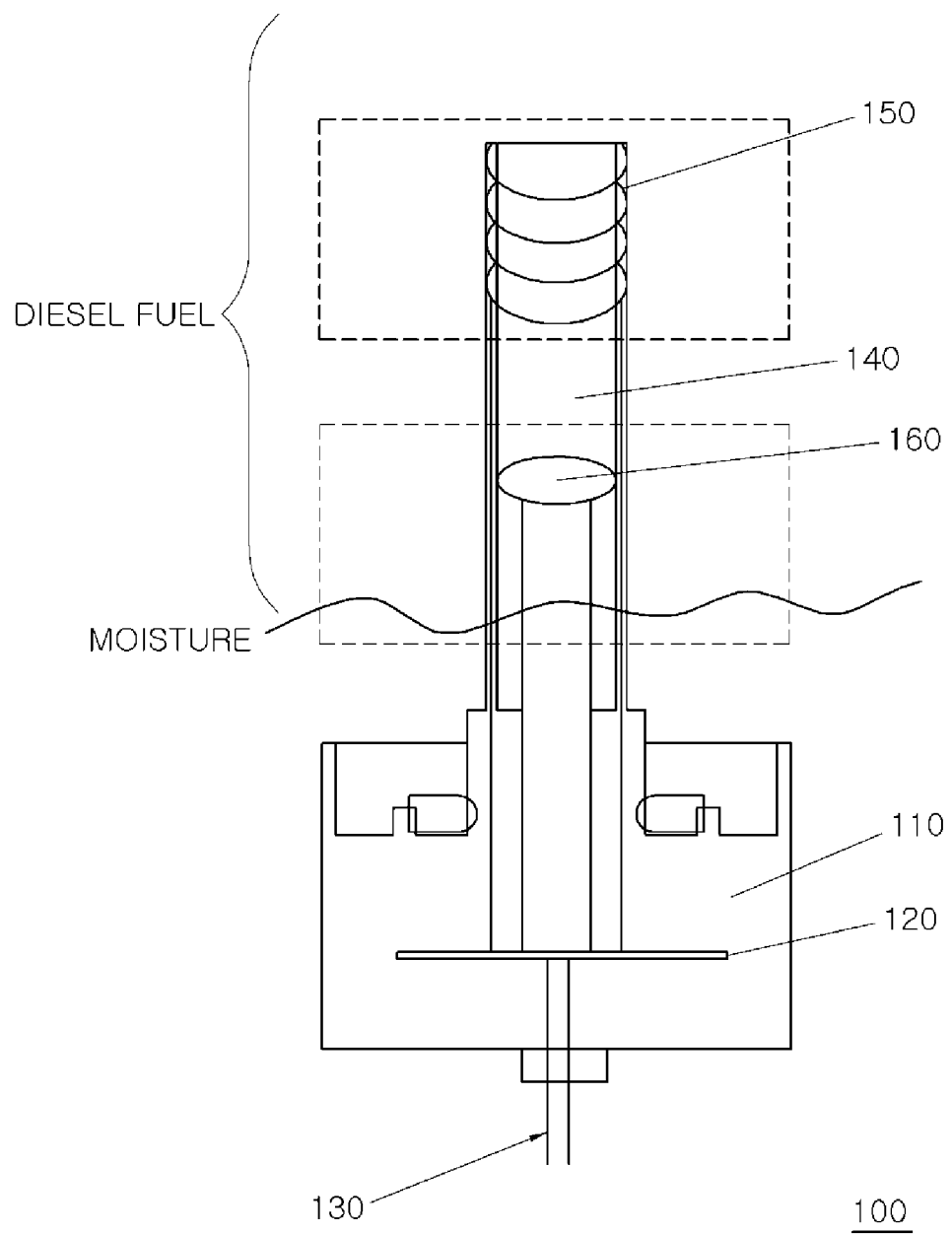
FIG. 2 is a cross-sectional view illustrating a diesel fuel quality inspection apparatus according to an exemplary embodiment of the present invention.

FIG. 2 is a cross-sectional view illustrating a diesel fuel quality inspection apparatus according to an exemplary embodiment of the present invention.

As shown in FIG. 2, a diesel fuel quality inspection apparatus according to an exemplary embodiment of the present invention includes a body portion 110 coupled to a lower end portion of a moisture storing part 20 of a diesel fuel filter, a guide portion 140 formed with a hollow type circular cylinder shape on a bottom surface in the body portion 110, and a first inspection portion formed to be fixed with a predetermined height in the guide portion 140.

A circuit portion 120 including a Printed Circuit Board (PCB) circuit board may be mounted in the body portion 110. The first inspection portion includes a coil member 150 wound as the predetermined number of coiling line along an inside circumference of the guide portion 140, and both end portions of the coil member 150 are connected with the circuit portion 120.

At this time, the coil member 150 is wound to the guide portion 140 with an insert injection type to form a coil structure.

A MOSFET-switch is formed at the circuit portion 120 to perform on or off of the switch per one second, wherein a voltage is supplied to the coil member 150.

At least one opening portion may be formed on an outside circumference surface of the guide portion 140, and moisture or diesel fuel collected by the filter portion 10 may be flowed into a hollow of the guide portion 140 through the opening portion. The opening may be formed to be extended in an axial direction of the guide portion 140.

Merely, it is desirable that diesel fuel flowed through the opening portion is positioned inside the coil member 150 wound along an inside circumference of the guide portion 140 and the height of coiling the coil member 150 is higher than a limit height collecting moisture which is a height that a moisture warning signal is generated by an after-mentioned second inspection portion.

The coil member 150 forms a magnetic field as diesel fuel positioned inside the coil member 150 is to be a medium when a voltage is supplied thereto by the circuit portion 120. At this time, as amount of the coil member 150 being magnetized is to be different depending on the medium positioned inside the wound coil member 150, permeability u, which is ratio of magnetized amount, is changed depending on the medium in the coil.

That is, permeability u is changed depending on diesel fuel as the medium, and in detail, permeability u is changed depending on amount of moisture contained to diesel fuel.

At this time, a relation between magneto-inductance and permeability is represented by the <equation 1> below, and thus magneto-inductance of the coil member 150 is changed to be proportionate to change of permeability.

$$L = \frac{\mu N^2 A}{l} \qquad \text{(equation 1)}$$

(L: inductance u: permeability N: the number of coiling line A: a cross-section of a coil l: a length of a magnetic circuit)

Therefore, as represented in the below mentioned <equation 2>, change of moisture contained to the medium to be diesel fuel is identified by measuring change of output voltage to be proportionate to the change rate of inductance and current.

$$V_{out} = L\frac{di}{di} \quad \langle \text{equation 2} \rangle$$

Figure 3:
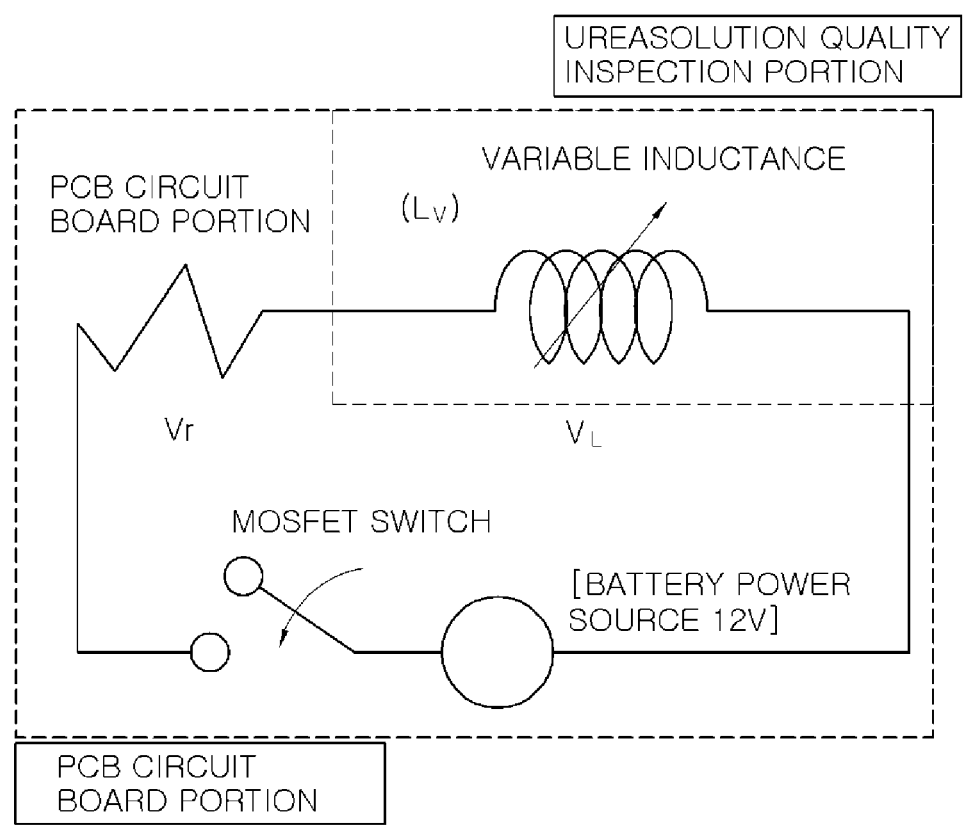
FIG. 3 is a circuit diagram illustrating a circuit portion of a diesel fuel quality inspection apparatus according to an exemplary embodiment of the present invention.

FIG. 3 is a circuit diagram illustrating a circuit portion 120 of a diesel fuel quality inspection apparatus according to an exemplary embodiment of the present invention.

Referring to FIG. 3, a power source of an outside battery 130 is connected with the circuit portion 120, and a logic for inspecting an output voltage is configured to be started at an on time of the switch by performing on or off of the MOSFET-switch formed at the circuit portion 120 per one second. Change of output voltage depending on change of magneto-inductance of the coil member 150 is measured by the circuit portion 120, and a control portion may determine whether to transmit a warning message to a person including a driver depending on change of output voltage measured from the circuit portion 120.

In further detail, an output voltage may be inspected according to the below mentioned <equation 3>.

$$V_L = V_{out} = V - V_R = Ve^{-\frac{R}{L}t} \quad \langle \text{equation 3} \rangle$$

(V: battery voltage R: fixed resistance L: inductance t: inspection time)

That is, magnetized amount of the coil member 150 is changed depending on change of amount of moisture contained to diesel fuel positioned inside the coil member 150 when a current is flowed to the coil member 150, and thus an output voltage is measured from the circuit portion 120 shown in FIG. 3 by change of inductance as magneto-inductance of the coil member 150 is changed.

At this time, the control portion which may mounted to be mounted in the body portion 110 identifies whether the output voltage is changed by checking the output voltage with real time. An optional limit value about change of the inductance is predetermined to a %, and then it is determined that there is faulty fuel having relatively large amount of moisture contained to diesel fuel in a case that the measured output voltage exceeds a voltage value when the inductance is changed as a % in comparison with a normal output voltage in normal diesel fuel, and thus the control portion is configured to determine to transmit a warning message to a person including a driver. The optional limit value a may be predetermined depending on amount of moisture allowed.

As shown in FIG. 2, a diesel fuel quality inspection apparatus according to an exemplary embodiment of the present invention may further include a second inspection portion transmitting a warning signal about amount of moisture which is collected in a diesel filter.

The second inspection portion is mounted in a hollow of the guide portion 140, and configured so that a first end thereof is electrically connected with the circuit portion 120 mounted in the body portion 110 and a current carrying portion 160 is positioned at a second end thereof. Therefore, a height of disposing the current carrying portion 160 is determined depending on a limit amount collecting moisture which is may be optionally predetermined.

A water surface of moisture stored in the moisture storing part 20 after being collected by a filter of the filter portion 10 is to be higher, and thus as a height of the water surface reaches the current carrying portion 160 of the second inspection portion so that the water surface is contacted with the current carrying portion 160, the circuit portion 120 generates a moisture warning signal by carrying a current.

Therefore, it is desirable that the second inspection portion is composed with a insulation material except the current carrying portion 160.

Figure 4:
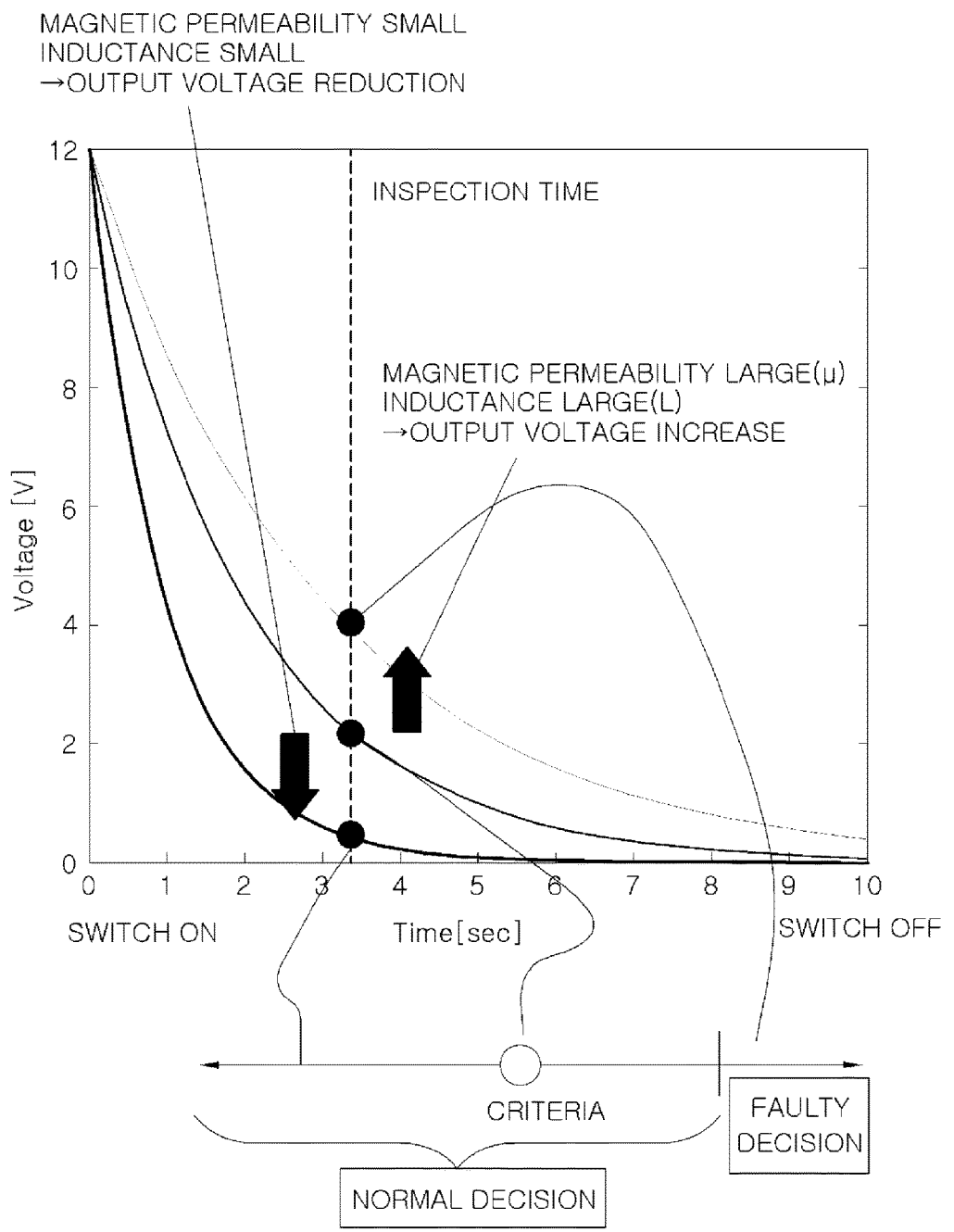
FIG. 4 is a rough graph about the standard of inspecting fault in a diesel fuel quality inspection method according to another exemplary embodiment of the present invention.

FIG. 4 is a rough graph about the standard of inspecting fault in a diesel fuel quality inspection method according to another exemplary embodiment of the present invention.

Figure 5:
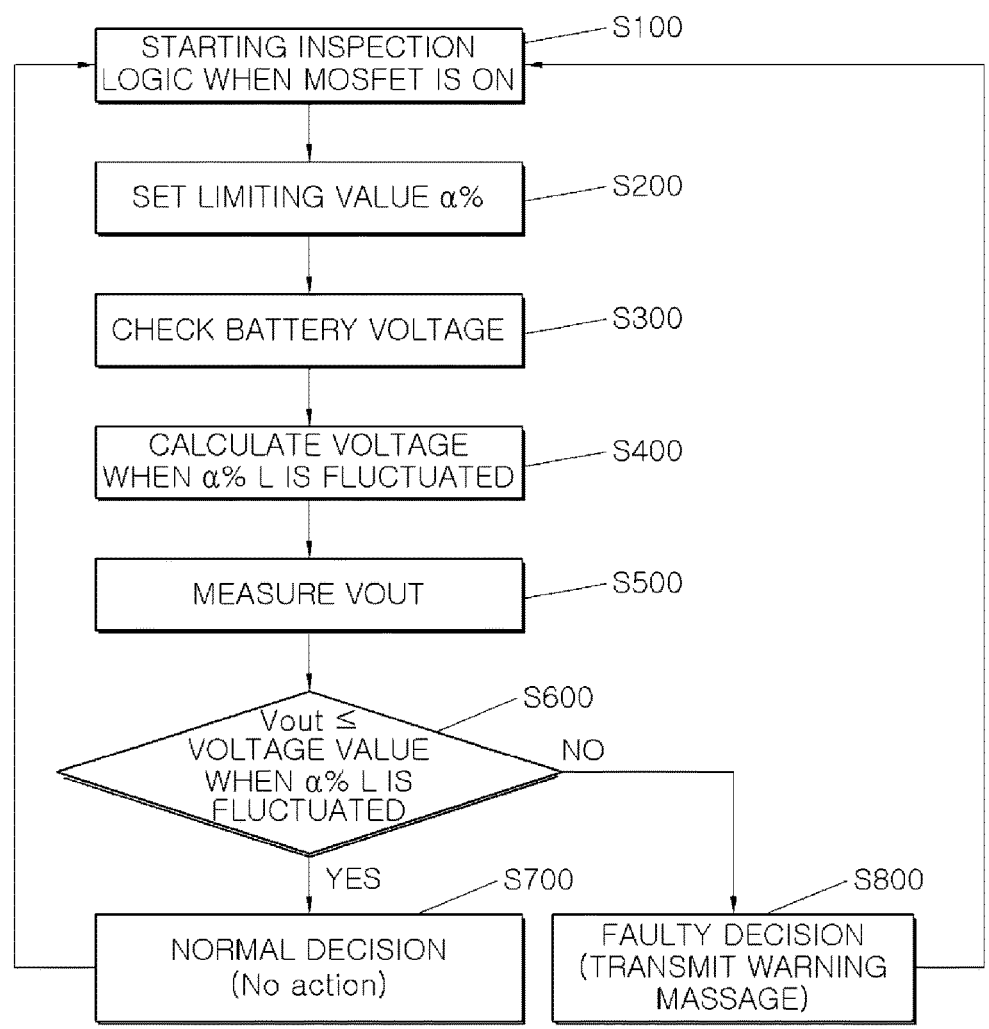
FIG. 5 is a flowchart illustrating a diesel fuel quality inspection method according to another exemplary embodiment of the present invention.

FIG. 5 is a flowchart illustrating a diesel fuel quality inspection method according to another exemplary embodiment of the present invention.

Hereinafter, a diesel fuel quality inspection method according to another exemplary embodiment of the present invention will be described referring FIG. 4 to FIG. 5.

A diesel fuel quality inspection method according to another exemplary embodiment of the present invention includes a step S100 of starting a inspection logic at an on time by performing on or off of a MOSFET-switch per one second, a step S200 of predetermining an optional limit value a % about change of inductance of a coil member, a step S300 of checking a battery voltage, a step S400 of determining a voltage value when inductance is changed as the a %, a step S500 of measuring an output voltage, a step S600 of determining whether the output voltage exceeds the voltage value determined at the step S400, a step S700 of deciding normal fuel in a case that the output voltage measured at the step S500 is lower than or same to the voltage value determined at the step S400 according to the result of the determination at the step S600, and a step S800 of deciding faulty fuel in a case that the measured output voltage is more than the voltage value determined at the step S400 according to the result of the determination at the step S600.

Both end portions of the coil member 150 are connected with the circuit portion 120, and an outside battery is connected with the circuit portion 120. A voltage is supplied to the coil member 150 by performing on or off of the MOSFET-switch formed at the circuit portion 120 per one second.

At this time, amount of magnetizing the coil member 150 is to be different depending on quality of diesel fuel positioned inside the coil member 150, that is to say amount of moisture contained to diesel fuel, wherein inductance value is changed. Therefore, the limit value a about change of inductance of the coil member 150 may be predetermined according to a degree that amount of moisture contained to diesel fuel is allowed.

When the limit value a is predetermined, a voltage value is determined when inductance is changed as the predetermined a %. In addition, an output voltage value, which is changed depending on quality of diesel fuel, that is to say amount of contained moisture, is measured to compare the measured output voltage value with the determined limit voltage value.

Because moisture, that is to say water has better permeability, magneto-inductance and output voltage of the coil member 150 are configured to be increased as represented in the equation 1 to equation 2 in a case that diesel fuel contains much moisture.

Therefore, as shown in FIG. 4, it is decided that present diesel fuel is normal fuel wherein amount of contained moisture is corresponded to a normal range in a case that the measured output voltage is lower than or same to the determined voltage value according to the result of comparing.

It is decided that present diesel fuel is faulty fuel wherein amount of contained moisture exceeds a normal range in a case that the measured output voltage is more than the determined voltage value according to the result of comparing.

At this time, the diesel fuel quality inspection method further includes a step of transmitting a warning message to a high rank controller by the control portion when It is decided that present diesel fuel is faulty fuel according to the result of determining.

For convenience in explanation and accurate definition in the appended claims, the terms "upper", "lower", "inner" and "outer", "up," "down," "upper", "lower," "upwards," "downwards", "front", "rear", "back", "inside", "outside", "inwardly," "outwardly," "interior", "exterior", "inner," "outer", "forwards" and "backwards" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A diesel fuel quality inspection apparatus, which is mounted to a lower end portion of a moisture storing part coupled to a lower portion of a filter portion and a filter portion for filtering foreign materials contained to fuel for inspecting moisture contained to diesel fuel to identify quality of fuel, including:
   a body portion coupled to the lower end portion of the moisture storing part;
   a guide portion formed with a hollow type circular cylinder shape on a bottom surface in the body portion; and
   a first inspection portion formed to be fixed with a predetermined height in the guide portion.

2. The diesel fuel quality inspection apparatus of claim 1, wherein the first inspection portion includes a coil member wound along an inside circumference of the guide portion.

3. The diesel fuel quality inspection apparatus of claim 2, wherein amount of the coil member being magnetized is to be different depending on quality of fuel positioned inside the wound coil member.

4. The diesel fuel quality inspection apparatus of claim 2, further including a circuit portion mounted in the body portion to measure change of output voltage depending on change of magneto-inductance of the coil member.

5. The diesel fuel quality inspection apparatus of claim 4, wherein first and second end portions of the coil member are respectively connected with the circuit portion.

6. The diesel fuel quality inspection apparatus of claim 4, further including a control portion determining whether to transmit a warning message depending on change of output voltage measured from the circuit portion.

7. The diesel fuel quality inspection apparatus of claim 1, wherein the guide portion includes at least one opening portion configured such that fuel or moisture is communicated into the guide portion.

8. The diesel fuel quality inspection apparatus of claim 2, wherein the circuit portion includes a MOSFET-switch repeating on or off per one second.

9. The diesel fuel quality inspection apparatus of claim 4, wherein a power source of an outside battery is connected with the circuit portion.

10. The diesel fuel quality inspection apparatus of claim 1, further including a second inspection portion mounted in the guide portion and configured so that a first end thereof is electrically connected with a circuit portion which is mounted in the body portion and a second end thereof is provided with a current carrying portion.

11. The diesel fuel quality inspection apparatus of claim 10, wherein the current carrying portion is formed to be positioned as a predetermined height apart from the circuit portion, and the circuit portion generates a moisture warning signal as the current carrying portion carries current during being contacted with a water surface of moisture collected to the moisture storing part.

12. A diesel fuel quality inspection method for inspecting quality of fuel by amount of moisture contained to fuel, including:
   starting an inspection logic at an on time by performing on or off of a MOSFET-switch per one second;
   predetermining an optional limit value a % about change of inductance of a coil member;
   checking a battery voltage;
   determining a voltage value when inductance is changed as the a %;
   measuring an output voltage;
   determining whether the output voltage exceeds the determined voltage value;
   deciding normal fuel in a case that the output voltage is lower than or equal to the determined voltage value according to the result of the determination; and
   deciding faulty fuel in a case that the measured output voltage is more than the determined voltage value according to a result of the determination.

13. The diesel fuel quality inspection method of claim 12, wherein amount of the coil member being magnetized is changed depending on quality of fuel positioned inside the wound coil member.

14. The diesel fuel quality inspection method of claim 12, wherein the value is predetermined depending on amount of moisture allowed in diesel fuel.

15. The diesel fuel quality inspection method of claim 12, further including transmitting a warning message in a case of deciding faulty fuel.

* * * * *